Figure 1:
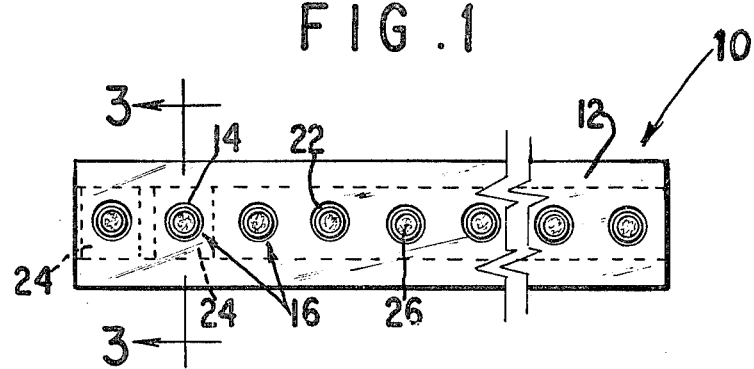

United States Patent [19]

D'Amato et al.

[11] 4,208,480
[45] Jun. 17, 1980

[54] **METHOD, REAGENTS AND APPARATUS FOR THE RAPID IDENTIFICATION OF *NEISSERIA GONORRHOEAE* AND *NEISSERIA MENINGITIDIS***

[75] Inventors: Richard F. D'Amato, Dix Hills; Louis A. Eriquez, Ronkonkoma, both of N.Y.

[73] Assignee: American Home Products Corporation, New York, N.Y.

[21] Appl. No.: 936,292

[22] Filed: Aug. 23, 1978

Related U.S. Application Data

[63] Continuation-in-part of Ser. No. 769,119, May 11, 1979, abandoned.

[51] Int. Cl.$^2$ .............................................. C12Q 1/04
[52] U.S. Cl. ..................................... 435/34; 435/300; 435/871
[58] Field of Search ................ 252/408; 195/100, 127; 435/34

[56] References Cited

U.S. PATENT DOCUMENTS

| | | | |
|---|---|---|---|
| 3,830,703 | 8/1974 | Beckford | 195/103.5 M X |
| 3,832,288 | 8/1974 | Rollender et al. | 195/103.5 M X |
| 3,957,584 | 5/1976 | Kronish et al. | 195/103.5 M |
| 4,026,767 | 5/1977 | Shih et al. | 195/103.5 M |
| 4,039,387 | 8/1977 | Simpson et al. | 195/103.5 M X |
| 4,048,016 | 9/1977 | Otto | 195/103.5 M X |

*Primary Examiner*—Raymond N. Jones
*Assistant Examiner*—Robert J. Warden
*Attorney, Agent, or Firm*—Joseph Martin Weigman

[57] ABSTRACT

The disclosure is directed to a method, reagents and apparatus for the rapid (one to four hours) identification of *Neisseria gonorrhoeae* and *Neisseria meningitidis* from cultures grown on a selective or a non-selective medium. One drop of growth suspended in sterile salt solution is placed in each of a plurality of miniature reaction chambers supported on a common base and incubated at 35°–37° C. for one to four hours. A dried substrate and buffer is contained in each chamber. A detector reagent such as a diazo dye in an aqueous solution with a polar solvent is added to each chamber after incubation. The color change in each chamber is noted and compared with a profile to identify *N. gonorrhoeae* and *Neisseria meningitidis*. Synthetic substrates rather than sugars are used in the reaction chambers. The substrates are naphthyl derivatives, β-naphthyl or β-naphthylamides, and are (1) β-naphthyl-β,D-galactopyranoside
(2) N-L-λ-glutamyl-β-naphthylamide
(3) L-hydroxyproline-β-naphthylamide
(4) L-serine-β-naphthylamide
(5) L-arginine-β-naphthylamide
(6) glycine-glycine-β-naphthylamide
(7) β-naphthyl-phosphate
(8) β-naphthyl-valerate
(9) 4 methoxy leucine-β-naphthylamide
(10) glycine-β-naphthylamide.

8 Claims, 3 Drawing Figures

METHOD, REAGENTS AND APPARATUS FOR THE RAPID IDENTIFICATION OF *NEISSERIA GONORRHOEAE* AND *NEISSERIA MENINGITIDIS*

This application is a continuation-in-part of Ser. No. 769,119, filed on May 11, 1979, now abandoned.

BACKGROUND OF THE INVENTION

This invention relates to a diagnostic system for microbial identification. More particularly, it relates to a process for the identification of Neisseria species, especially *N. gonorrhoeae* and *N. meningitidis*. It further relates to the reagents for use in the process and to apparatus for carrying out the process, including a test strip made of a number of small receptacles or reaction chambers each containing a synthetic substrate and a buffer and being adapted to contain a test inoculum during incubation.

The incidence of gonorrhea has reached epidemic proportions. About three million cases of gonorrhea occurred in the United States during 1975. A system for the rapid identification of *N. gonorrhoeae* will be a major aid in the identification of the infection and the subsequent treatment of the patient. The term "gonorrhea" encompasses all infections caused by the gonococcus *Neisseria gonorrhoeae*.

The increased isolation of *N. gonorrhoeae* from non-genital sites, as well as the isolation of *N. meningitidis* and *N. lactamica* from genital sites presents a problem in the clinical laboratory. All of these species of Neisseria will grow on media used for the isolation of *N. gonorrhoeae*. Therefore, isolates must be further characterized to ascertain the identity of the organism.

The conventional techniques for the identification of *N. gonorrhoeae* require the culturing of a specimen on a selective medium followed by an ozidase test, a gram stain and a morphology study to make a presumptive identification of *N. gonorrhoeae*.

Confirmation of the identification by conventional techniques requires further incubation on a non-selective enrichment medium, such as a chocolate agar plate, to obtain sufficient growth for the confirmatory tests. Incubation for 18 to 24 hours is required to obtain sufficient growth. The growth from the foregoing medium is inoculated to carbohydrate degradation medium which usually consists of a battery of the carbohydrates: glucose (dextrose), maltose, sucrose, fructose, levulose and lactose sugars in cystine-trypticase agar base with phenol red indicator. They are incubated in aerobic conditions as required for carbohydrate degradation for up to two days during which time the carbohydrates may be converted into acidic end products. The presence of acid is detected by the change in color of an indicator, such as phenol red, from red to yellow, which indicates a positive reaction. The conventional technique for confirmation can require up to three days.

Some processes are known for a more rapid identification of *N. gonorrhoeae*. The known rapid processes utilize a primary isolation on a selective medium, as in the conventional technique, followed by inoculation of a primary isolation plate to grow the inoculum. The carbohydrate degradation media are then inoculated with a very dense suspension of the bacteria and incubated in a water bath for up to 5 hours to produce an acid reaction. That is, they use a small amount of the substrate, and a very dense bacteria suspension and accelerate the reaction. The processes do not depend on the growth of the organism under these conditions but depend on the presence of preformed enzyme that will degrade the various substrates.

THE PRIOR ART

The modified Thayer-Martin (MTM) medium has been widely accepted for primary isolation of the gonococcus and meningococcus from sites where these organisms are far outnumbered by natural bacterial flora (Thayer, J. D., and Martin, J. E., Jr.: Improved Medium Selective for the Cultivation of *N. gonorrhoeae* and *N. meningitidis*. Public Health Rep. 81: 559–562, June 1966). In the T-M medium overgrowth by gram-positive and gram-negative bacteria is prevented by the addition of vancomycin to inhibit gram-positive contaminants, sodium colistimethate for the gram-negative flora and nystatin to inhibit yeast, which is sometimes a nuisance in vaginal and rectal cultures. The MTM medium, because it contains antimicrobial agents, suppresses the growth of bacteria and fungi and Neisseria other than *N. gonorrhoeae*, *N. meningitidis* and *N. lactamica*.

Specimens suspected to contain a gonococcus (GC) or meningococcus are plated on an MTM medium and incubated in carbon dioxide at 35° C. for up to three days. Isolates are selected from the growth for positive identification. However, the identification of organisms after isolation on the MTM medium remains cumbersome and time consuming. Purification takes 24 hours, followed by an additional 5 to 48 hour period for identification. Thus, the identification (after isolation on MTM) requires a minimum of approximately 30 hours and sometimes four days depending on the fastidiousness of the organism and the nature of the identification tests used.

After the isolation on the MTM medium, an enrichment medium, typically a chocolate agar plate, is inoculated and incubated for 18 to 24 hours to obtain sufficient growth of inoculum for confirming tests. Once sufficient growth is available an inoculum of the growth in water is made and used to inoculate a carbohydrate degradation medium which usually consists of a battery of glucose, sucrose, fructose, and the like, sugars. The purpose of the carbohydrate degradation is to produce acid from glucose and other sugars when tested in cystine-Trypticase agar (CTA) medium.

A more rapid system for the identification of *N. gonorrhoeae* was developed by Kellogg and Turner. (Kellogg, D. S., Jr. and E. M. Turner, 1973. Rapid Fermentation Confirmation of *Neisseria Gonorrhoeae*. Appl. Microbiol. 25: 550–552.)

With the CTA system using CTA sugars incubation in air is carried out at 35° C. to promote the growth of the organism. As the organism grows it elaborates an enzyme which will break down the sugar. As it breaks down the sugar, acid end products are produced. The presence of an acid is detected by an indicator. In the Kellogg system the growth of the organism was incidental, and the purpose was to detect the preformed enzyme which should be already present. The Kellogg system makes use of a small amount of substrates consisting the same carbohydrate sugars used in the CTA tests. Kellogg uses dense cell suspensions and buffered salt solution to more rapidly detect acidification. Confirmation of the culture as *N. gonorrhoeae* is available within five hours after a purification plate is successfully inoculated with a suspected colony from MTM and incubated for 18 to 24 hours.

Complicating factors of both growth and non-growth carbohydrate digestion tests are that maltose frequently contains excessive amounts of contaminating, readily fermentable substances which will give false positives. Also, subculture of isolated colonies from MTM to chocolate plates is necessary in order to achieve sufficient growth for a heavy inoculum.

In the Kellogg procedure only glucose, maltose, sucrose are used and fructose is omitted. The glucose degradation only would characterize an isolate as being *N. gonorrhoeae* whereas the additional degradation of maltose and no other carbohydrate would indicate *N. meningitidis*. Lactose is degraded only by *N. lactamica* which distinguishes it from *N. meningitidis*. An improvement in the Kellogg method was described by W. Jerry Brown (Brown, W. J. 1974. Modification of the Rapid Fermentation Test for *Neisseria gonorrhoeae*. Appl. Microbiol. 27:1027–1030.) Brown modified the buffer-salt solutions and used a heavier inoculum to provide a method which produced positive identification within 4 hours. The Brown modification of the Kellogg method utilized the same naturally occurring substrates as Kellogg.

Recently a method of making a positive identification in 1 to 4 hours has been described (Morse S. A. and L. Bartenstein, 1976. Adaptation of the Minitek System for Rapid Identification of *Neisseria gonorrhoeae*. J. Clin. Microbiol. 3:8–13). Minitek produces and markets microtiter plates which contain shallow wells. Into each of the wells is placed a disc which contains natural substrates in the dry state. The carbohydrates are again glucose, maltose, lactose and sucrose as have been traditionally used. The wells are inoculated with a dense suspension of bacteria obtained from a purification plate. The Minitek system is based upon the production of acid from the carbohydrates and utilizes the buffer sodium bicarbonate to facilitate the reading of negative reactions. The discs employed in the Morse et al. paper above used as substrates dextrose-nitrate, dextrose, maltose, lactose, and o-nitrophenyl-$\beta$-galactopyranoside, (ONGP). At very high cell densities (greater than $5.0 \times 10^9$ colony-forming units per milliliter) positive reactions could be read within 30 minutes. Ninety percent of the isolates produced detectable acid from glucose within 4 hours. All isolates were identified by 6 hours. All isolates identified with the CTA medium were also identified by the Minitek system. In addition, the Minitek procedure identified more isolates of *N. gonorrhoeae* and *N. meningitidis* than were identified with CTA medium. Some false negative reactions occasionally were observed, often due to an inoculum with a low cell density. False negative reactions were encountered when inocula were prepared directly from Transgrow medium or the T-M plate used in the initial isolation of the organism. Morse overcame the problem by restreaking isolates on one half of a GC agar plate and incubating overnight. The Minitek process requires an inoculum from a purification plate incubated for 18 to 24 hours.

The ONPG reaction is usually thought of as equivalent to lactose fermentation. If an organism has the ability to hydrolyze the ONPG substrate and give a color change, it usually is lactose positive in CTA sugar fermentations for lactose. *N. lactamica* is the only Neisseria of interest that can be differentiated from *N. meningitidis* and *N. gonorrhoeae* that has the ability to hydrolyze both the synthetic ONPG and ferment lactose in a conventional sugar fermentation test.

Three organisms are usually capable of growing on MTM medium, *N. gonorrhoeae*, *N. meningitidis*, *N. lactamica*. *N. gonorrhoeae*, and *N. meningitidis* are usually classified as the only two pathogens of the Neisseria. *N. lactamica* is usually isolated and is usually a saprophyte. The differentiation of *N. meningitidis* from *N. lactamica* is based on lactose degradation or the ONPG test. Both *N. meningitidis* and *N. lactamica* can degrade glucose and maltose. They both are oxidase-positive organisms, gram-negative diplococci capable of growing on MTM medium. The differential test between *N. meningitidis* and *N. lactamica* is the ONPG test or the lactose degradation test. *N. lactamica* can hydrolyze ONPG and breakdown or degrade lactose; *N. meningitidis* cannot.

Other species of Neisseria can possibly grow on MTM medium but usually do not. However, if they do grow on MTM, with existing technology they are easily differentiated from *N. gonorrhoeae*, *N. meningitidis*, *N. lactamica* by carbohydrate degradation tests. Branhamella and Moraxella species also can grow on MTM medium but usually do not. If they do, they can be differentiated from *N. gonorrhoeae*, *N. meningitidis* and *N. lactamica* by the fact that these organisms do not degrade any carbohydrates and produce acid. They were investigated to determine their enzymatic pattern with the synthetic substrates in the present invention. Morphologically, they are similar to Neisseria, and they are oxidase-positive.

DESCRIPTION OF THE INVENTION

The objects of the present invention may be achieved with a device for the rapid identification of microorganisms comprising a supporting base, a plurality of miniature reaction chambers fixedly supported by said base, a dried substrate disposed in each of said reaction chambers, said substrates being present in the amount of 25 to 50 nanomoles per reaction chamber and consisting of an amino acid coupled to a chromogen, and a dried buffer disposed in each of said reaction chambers and consisting of 1 to 500 nanomoles of a buffer selected from a class consisting of tris-HCl, tris-malate and phosphate buffer containing $K_2HPO_4, KH_2PO_4$ and a polyvinyl alcohol, whereby upon the addition of diazo dye in an aqueous solution with a polar solvent as a detector agent and an inoculum to be identified, and incubation for up to five hours at 35° C., the microorganism may be identified by comparing the positive and negative reactions occurring with a predetermined identification chart.

The objects of the invention with regard to particular microorganisms may be achieved with a device for the rapid identification of *Neisseria gonorrhoeae* and *Nesseria meningitidis* comprising a supporting base, a plurality of miniature reaction chambers fixedly supported by said base a dried substrate disposed in each of said reaction chambers consisting of 25 to 50 nanomoles per chamber of an amino acid naphthylamide, and from 1 to 500 nanomoles per chamber of a buffer.

The method of the present identification differs from the prior art in the utilization of synthetic substrates rather than naturally occurring substrates or in the application of specific colorimetric substrates. The substrates are selectively hydrolyzed by enzymes during incubation. These enzyme activities have not been applied for use in identification of Neisseria in microbiology. The enzyme classes may be amino peptidases, lipases, phosphatases, phosphodiesterases, arylamino acid hydrolases, aryl and alkyl amidases and glycosidases.

The process of the present invention permits the identification of *N. gonorrhoeae* more rapidly than either the conventional technique or the known rapid processes. In the process of the invention, a specimen is inoculated on a selective medium, such as the MTM medium. The purification step of growth on a non-selective medium, such as chocolate agar, is eliminated. When growth is detected on the selective medium, inoculation is made onto a synthetic substrate. The present invention is based on enzymatic reactions utilizing chromogenic substrates. The synthetic substrates used in the present process are commercially available. As the organism hydrolyzes the synthetic substrates, a product is released which can be detected by an indicator.

The substrates which are used in the practice of the invention are the following:

| Substrates | Enzyme Detected | Enzyme Abbreviations |
|---|---|---|
| (1) $\beta$-naphthyl-$\beta$,D-galactopyranoside | $\beta$-galactosidase | BGAL |
| (2) N-L-$\lambda$-glutamyl-$\beta$-naphthylamide | $\lambda$-glutamyl aminopeptidase | $\lambda$GAM |
| (3) L-hydroxyproline-$\beta$-naphthylamide | hydroxyproline aminopeptidase | OHPAP |
| (4) L-serine-$\beta$-naphthylamide | serine aminopeptidase | SAP |
| (5) L-arginine-$\beta$-naphthylamide | arginine aminopeptidase | AAP |
| (6) glycine-glycine-$\beta$-naphthylamide | glycyl-glycine aminopeptidase | GAP |
| (7) $\beta$-naphthyl-phosphate | acid phosphatase | AP |
| (8) $\beta$-naphthyl-valerate | valerase | VAL |
| (9) 4-methoxyleucine-$\beta$-naphthylamide | 4-methoxyleucine aminopeptidase | 4-LEU |
| (10) glycine-$\beta$-naphthylamide | glycine aminopeptidase | GLY |

Substrate stock solutions are prepared by dissolving the substrate in a 0.1 M solution of a salt of Tris (hydroxy-methyl) aminomethane (hereafter abbreviated "TRIS") containing 0.5 percent by weight of polyvinyl alcohol (PVA), and buffering to a predetermined pH as shown in Table B.

Table B

| Substrate | TRIS Salt | Preferred pH | pH Range |
|---|---|---|---|
| 1 | TRIS-HCl | 6.8 | 5.0–7.9 |
| 2 | TRIS-Malate | 7.6 | 6.3–8.3 |
| 3 | TRIS-Malate | 7.2 | 6.3–8.0 |
| 4 | TRIS-Malate | 7.2 | 6.3–7.5 |
| 5 | TRIS-Malate | 8.0 | 6.8–8.4 |
| 6 | TRIS-Malate | 8.0 | 6.8–8.4 |
| 7 | TRIS-HCl | 5.5 | 5.2–5.8 |
| 8 | TRIS-Malate | 7.6 | 6.5–8.1 |
| 9 | TRIS-Phosphate | 7.6 | 6.0–8.1 |
| 10 | TRIS-Phosphate | 8.0 | 6.8–8.4 |

All substrate stock solution are in a concentration of $1 \times 10^{-3}$ molar (M). Fifty microliters of each of the substrate solutions is dispensed in a cupule on a test strip. Preferably, an indicium is printed on the test strip identifying the enzyme which is to be formed in the adjacent cupule. The final concentrations of the reagents in each cupule are $0.05 \times 10^{-6}$ moles of the substrate and $5.0 \times 10^{-6}$ moles of the Tris buffer. The strips are dried under vacuum or in air below 50° C. When dried, the substrate and the pads adhere to a porous backing.

The following buffers are suitable as substitutes for the Tris and phosphate buffers.

1. TES-N-tris-(hydroxymethyl)methyl-3-aminopropane sulfonate
2. HEPES-N-2-hydroxyethylpiperazine-N'-2-ethane sulfonate
3. HEPPS-N-2-hydroxyethylpiperazine-N'-3-propane sulfonate
4. CHES-cyclohexylaminoethane sulfonic acid
5. CARBONATE-sodium or potassium carbonate
6. BORATE-sodium or potassium borate Buffers are prepared in aqueous solution containing 0.2% PVA to yield a final concentration of 0.5 M after pH adjustment.

Preferably each of the ten substrates is placed in a separate cupule of a test strip such as is shown in the drawings.

Figure 2:
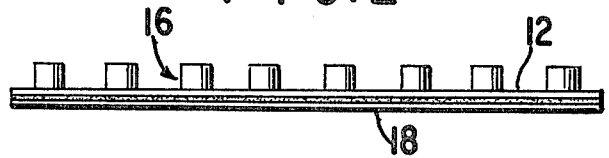

FIG. 1 is a perspective view of a biochemical test strip having ten individual reaction chambers; and FIG. 2 is a perspective view of one of the individual reaction chambers.

Figure 3:
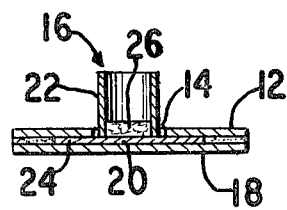

The test strip 10 is made up of a rigid upper member 12 having a plurality of openings 14 in which is inserted a reaction chamber, or cupule, 16 which is held in place by a backing member 18, which may be joined together by adhesive or thermally fused where both are formed from suitable material, such as thermoplastic resin. The reaction chamber, or cupule, structure is shown in FIG. 3. There the cupule 16 has a base 20 and a wall 22 which in the preferred embodiment is round. A flange 24 is formed around the base, preferably with a bent-up peripheral annulus. The flange is engaged between the upper member 12 and the backing member 18 and serves to hold the cupule firmly in place in the assembled test strip. A pad 26 is fastened in the bottom of the cupule 16. The pad is preferably of white cellulose wadding, but may be polyvinyl chloride polymer or other suitable materials which are inert to the reaction to be carried out. In a particularly advantageous embodiment, the test strip is about 10 centimeters long by 2 centimeters wide. Each of the cupules is 50 millimeters in diameter and provides 50 millimeters freeboard above the top of the pad.

Substrates are used at approximately $1.0 \times 10^{-3}$ M. The exact concentration of each substrate should be such that at least 25–50 nanomoles are available per cupule.

The detector reagents are prepared immediately prior to each test from the following detector stock solution. The detector reagent is formed by mixing 10.0 ml of the detector stock solution with 0.4g of fast blue BB (Na Salt). The detector reagent should not be exposed to bright light after mixing and must be used within 1 hour after mixing.

Detector Stock Solution

| Tris base | 175 gr |
|---|---|
| Sodium Lauryl sulfate | 50 gr |
| Hydrochloric acid 37% | 55 ml |

| | |
|---|---|
| -continued | |
| 2-Methoxy ethanol | 500 ml |
| Water | 500 ml |

2 methoxy ethanol added after solids dissolved

The following diazonium dye reagents have been shown to react in a specific manner with the B-naphthyl or B-naphthylamine released by enzyme from the substrates:

(1) Fast Red PDC
(2) Fast Red B
(3) Fast Red AL
(4) Fast Red TR
(5) Fast Blue RR
(6) Fast Garnet GBC
(7) Fast Blue B
(8) Fast Scarlet CG
(9) Fast Violet B
(10) Kiazo Red RC
(11) Fast Black K
(12) 0-diansidine The reaction of the above dyes with naphthylamine and naphthyl has been shown in our laboratory and established in the literature (Biological Stains, H. J. Conn. Williams and Wilkins 1961). Each dye is dissolved in the detector reagent stock solution yielding 0.4g/10ml.

A typical example of the use of any of the above dyes consists of the preparation, inoculation, and incubation of strips as described. A. 0.5g portion of any dye listed above or fast blue BB is dissolved in 10 ml of stock detector solution. One to two drops of the above solution is added to each cupule. The reaction is allowed to proceed for 10 minutes at room temperature. A change in color from a negative control is considered a positive reaction. The absence of color change is a negative reaction. The pattern observed is compared to Table A and the organism identified by comparison.

In Table A, the first line opposite each organism shows the number positive and the number tested as a fraction, the second line shows the percent positive reactions and the third line characterizes the reaction by a symbol. The symbol "—" indicates a predominantly negative reaction; the symbol "+" indicates a predominantly positive reaction, and the symbol "V" indicates a variable reaction.

Identification of the microorganism is accomplished by detecting the chromogen released from the substrate by enzymatic cleavage. The range of detection is from 5 to 40 nanomoles of chromogen. The reaction typically proceeds as follows:

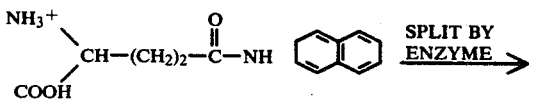

N—L-λ-glutamyl-β-nathylamide

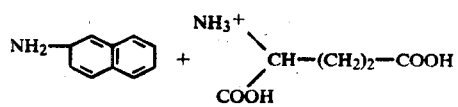

β-napthylamine + λ-glutamic acid

Fast Blue BB
(colorless or
pale yellow)

DIAZO DYE (deep violet or orange)

Classes of enzymes involved in the test system are:
1. Glycosidases
2. Aminopeptidases (Arylamidase) (Hydrolytic Aminotransferases)
3. Phosphatases
4. Carboxylases With regard to the location of enzymes in relation to bacterial cell; the detectable enzymes can be either extracellular, periplasmic, or cell bound. Enzymes liberated by autolysis are also detectable.

It should be noted that the assays used in the test system measures the sum of the activities of a class of enzyme rather than a single enzyme entity. A color change from pale yellow to violet or orange indicates a positive reaction.

The following examples require a single colony to be tested to be 2 millimeters or larger in size.

EXAMPLE I

This example illustrates one method of identifying N. gonorrhoeae.

At least 2 mm of growth from single large colony of suspected N. gonorrhoeae is suspended in 0.5 ml of sterile 0.85 percent sodium chloride with 0.05 percent calcium chloride and 0.05 percent sodium bicarbonate in water. The growth can be obtained from modified Thayer-Martin medium (MTM), Chocolate sugar (CA), NYC medium (NYC), or Transgro medium (TM) after 24 hours incubation (primary isolation plate). One drop of suspension is used to perform a conventional oxidase test and gram stain. The remainder is inoculated into the cupules of test strip, one drop of suspension per cupule. The test strip is incubated in a humid covered plastic chamber at 35–37C for 1 hour.

One drop of detector reagent is placed in each cupule of the test strip. The reaction is allowed to proceed for 10 minutes at room temperatures. Identification of the microorganism is made by comparing the color of the reaction mass with Table A.

EXAMPLE II

This example illustrates an alternate method of identifying N. gonorrhoeae.

Bacterial growth is removed from the surface of an enriched Chocolate agar plate, a Thayer-Martin medium (MTM), or a similar Neisseria-permissive medium after growth for 18 to 24 hours at 35° C. in 5.0% carbon dioxide and is suspended in 0.85% sodium chloride solution. The suspension is adjusted to a MacFarland No. 3 nepthalometer standard with 0.85% sodium chloride solution. Then 20 to 50 microliters of this suspension is used as an inoculum into each of the cupules of the test strip for enzymatic analysis.

The test strip is incubated in a humid enclosed chamber at 35° to 37° C. for one hour. One drop of detector reagent is placed in each cupule of the test strip. The reaction is allowed to proceed for 10 minutes at room temperatures. Identification of the microorganism is made by comparing the color of the reaction mass with Table A.

EXAMPLE III

This example illustrates an alternate method of identification of a suspected *N. gonorrhoeae* colony.

In this method a phosphate buffer, pH 7.3 is substituted for the 0.1 M TRIS-Malate, pH 8.0. The phosphate buffer contains per liter:

| | |
|---|---|
| $K_2HPO_4$ | 4.0 g |
| $KH_2PO_4$ | 1.0 g |
| Polyvinyl Alcohol (PVA) | 5.0 g |

As an alternate the substrates may be dissolved in distilled water, the buffer incorporated into the medium.

A single colony of suspected *N. gonorrhoeae* is removed from a primary isolation plate, preferably an MTM plate. The colony diameter should be greater than 1.5 millimeters. The colony is vigorously suspended in a growth medium containing the following ingredients per liter.

| | |
|---|---|
| Proteose Peptone #3 | 7.0 g |
| Glucose | 4.0 g |
| $K_2HPO_4$ | 4.0 g |
| $KH_2PO_4$ | 1.0 g |
| $NaHCO_3$ | 0.5 g |
| IsoVital X (Difco, BBL) | 10.0 ml |

The medium described by R. T. Jones and R. S. Talley (J. Clin. Microbiol. 1977. 5:9–14) may be substituted for the above medium. Any medium supporting the rapid growth of neisseria which is colorless can be used.

Twenty to forty microliters of the inoculated medium is placed in contact with the substrate solutions.

TABLE A

| Organism | Number Tested | B-GAL 1 | λGAM 2 | OHPAP 3 | AAP 4 | SAP 5 | GAP 6 | AP 7 | VAL 8 | 4-LEU 9 | GLY 10 | API CODE |
|---|---|---|---|---|---|---|---|---|---|---|---|---|
| *N. gonorrhea* | 37 | 0/37 | 0/37 | 37/37 | 36/37 | 1/37 | 3/37 | 0/37 | 36/37 | 19/37 | 7/37 | |
| | | 0 | 0 | 100 | 97.2 | 2.7 | 8.1 | 0 | 97.2 | 45.9 | 18.9 | |
| | | – | – | N. flavescens | + | – | – | – | + | v | v | v |
| *N. meningitidis* | 16 | 0/16 | 16/16 | 1/16 | 16/16 | 3/16 | 11/16 | 4/16 | 6/16 | 15/16 | 15/16 | |
| | | 0 | 100 | 6.2 | 100 | 18.7 | 68.7 | 25 | 40 | 100 | 93.3 | |
| | | – | + | – | N. flava | flava | – | v | v | v | + | + |
| *N. actamica* | 15 | perflave | N. perflava | 15/15 | 14/15 | 14/15 | 14/15 | 14/15 | 5/15 | 15/15 | 14/15 | |
| | | 100 | 0 | N. subflava | 93 | 93 | 93 | 33.3 | 100 | 93 | | |
| | | + | – | + | + | + | + | v | +b. catarrhalis | + | + | |
| *N. mucosa* | 11 | 0/11 | 0/11 | 11/11 | 11/11 | 10/11 | 9/11 | 11/11 | 0/11 | 10/11 | 11/11 | |
| | | 0 | 0 | 100 | 100 | 91 | 82 | 100 | 0 | 91 | 100 | |
| | | – | – | + | + | + | + | + | – | + | + | |
| *N. sicca* | 7 | 0/7 | 0/7 | 6/7 | 7/7 | 6/7 | 1/7 | 6/7 | 1/7 | 7/7 | 7/7 | |
| | | 0 | 0 | 86 | 100 | 86 | 14 | 86 | 14 | 100 | 100 | |
| | | – | – | + | + | + | v | + | – | + | + | |
| *N.flavescens* | 5 | 0/5 | 0/5 | 5/5 | 5/5 | 5/5 | 5/5 | 0/5 | 0/5 | 5/5 | 5/5 | |
| | | 0 | 0 | 100 | 100 | 100 | 100 | 0 | 0 | 110 | 100 | |
| | | – | – | + | + | + | + | – | – | + | + | |
| *N.flava* *N.perflava* *N.subflava* | 17 | 0/17 | 0/17 | 17/17 | 16/17 | 15/17 | 4/17 | 2/17 | 17/17 | 16/17 | 17/17 | |
| | | 0 | 0 | 100 | 94 | 88 | 23 | 12 | 100 | 94 | 100 | |
| | | – | – | + | + | + | v | v | + | + | + | |
| *b.catarrhalis* | 8 | 0/8 | 0/8 | 3/8 | 8/8 | 8/8 | 8/8 | 0/8 | 7/8 | 8/8 | 8/8 | |
| | | 0 | 0 | 37.5 | 100 | 100 | 100 | 0 | 87.5 | 100 | 100 | |
| | | – | – | v | + | + | + | – | + | + | + | |
| TM-1 | 6 | 0/6 | 0/6 | 6/6 | 6/6 | 0/6 | 6/6 | 0/6 | 0/6 | 6/6 | 6/6 | |
| | | 0 | 0 | 100 | 100 | 0 | 100 | 0 | 0 | 100 | 100 | |
| | | – | – | + | + | – | + | – | – | + | + | |
| M-3 | 3 | 0/3 | 0/3 | 2/3 | 3/3 | 1/3 | 1/3 | 3/3 | 2/3 | 3/3 | 3/3 | # Pos. |
| | | 0 | 0 | 67 | 100 | 33 | 33 | 100 | 67 | 100 | 100 | % Pos. |
| | | – | – | v | + | v | v | + | v | + | + | Reaction |
| M-4 | 6 | 0/6 | 6/6 | 0/6 | 6/6 | 0/6 | 0/6 | 0/6 | 0/6 | 0/6 | 0/6 | # Pos. |
| | | 0 | 100 | 0 | 100 | 0 | 0 | 0 | 0 | 0 | 0 | % Pos. |
| | | – | + | – | + | – | – | – | – | – | – | Reaction |
| M-5 | 6 | 0/6 | 0/6 | 6/6 | 6/6 | 6/6 | 6/6 | 0/6 | 0/6 | 6/6 | 6/6 | # Pos. |
| | | 0 | 0 | 100 | 100 | 100 | 100 | 0 | 0 | 100 | 100 | % Pos. |
| | | – | – | + | + | + | + | – | – | + | + | Reaction |
| M-6 | 3 | 0/3 | 0/3 | 3/3 | 0/3 | 0/3 | 0/3 | 0/3 | 0/3 | 3/3 | 0/3 | # Pos. |
| | | 0 | 0 | 100 | 0 | 0 | 0 | 0 | 0 | 100 | 0 | % Pos. |
| | | – | – | + | – | – | – | – | – | + | – | Reaction |
| *M. osloensis* | 6 | 0/6 | 0/6 | 1/6 | 6/6 | 0/6 | 6/6 | 6/6 | 6/6 | 6/6 | 6/6 | # Pos. |
| | | 0 | 0 | 16.6 | 100 | 0 | 100 | 100 | 100 | 100 | 100 | % Pos. |
| | | – | – | v | + | – | + | + | + | + | + | Reaction |
| *M. nonliquefaciens* | 5 | 0/5 | 0/5 | 0/5 | 5/5 | 3/5 | 5/5 | 5/5 | 2/5 | 5/5 | 5/5 | # Pos. |
| | | 0 | 0 | 0 | 100 | 60 | 100 | 100 | 40 | 100 | 100 | % Pos. |
| | | – | – | – | + | v+ | + | + | + | + | + | Reaction |

TABLE A-continued

| Organism | Number Tested | B-GAL 1 | λGAM 2 | OHPAP 3 | AAP 4 | SAP 5 | GAP 6 | AP 7 | VAL 8 | 4-LEU 9 | GLY 10 | API CODE |
|---|---|---|---|---|---|---|---|---|---|---|---|---|
| *M. facunata* | 4 | 0/4 | 0/4 | 0/4 | 0/4 | 0/4 | 0/4 | 4/4 | 0/4 | 4/4 | 4/4 | # Pos. |
| | | 0 | 0 | 0 | 0 | 0 | 0 | 100 | 0 | 100 | 100 | % Pos. |
| | | − | − | − | − | − | − | + | − | + | + | Reaction |
| *M. phenylpyruvica* | 2 | 0/2 | 0/2 | 0/2 | 0/2 | 0/2 | 0/2 | 0/2 | 2/2 | 2/2 | 0/2 | # Pos. |
| | | 0 | 0 | 0 | 0 | 0 | 0 | 0 | 100 | 100 | 0 | % Pos. |
| | | − | − | − | − | − | − | − | + | + | − | Reaction |
| *M. kingii* | 2 | 0/2 | 0/2 | 2/2 | 0/2 | 0/2 | 2/2 | 2/2 | 2/2 | 2/2 | 2/2 | # Pos. |
| | | 0 | 0 | 100 | 0 | 0 | 100 | 100 | 100 | 100 | 100 | % Pos. |
| | | − | − | + | − | − | + | + | + | + | + | Reaction |

What is claimed is:

1. A method for the rapid identification of microorganisms comprising the steps of:
   a. Adding a predetermined amount of a salt solution containing a microorganism to be identified to a solution containing a diazonium dye detector reagent in an aqueous solution with a buffer, and a substrate and incubating at about 35° C. for up to five hours and comparing the positive and negative reactions with an identification chart, said substrate being selected from the group consisting of:
      (1) β-naphthyl-β,D-galactopyranoside
      (2) N-L-λ-glutamyl-β-naphthylamide
      (3) L-hydroxyproline-β-naphthylamide
      (4) L-serine-β-naphthylamide
      (5) L-arginine-β-naphthylamide
      (6) glycine-glycine-β-naphthylamide
      (7) β-naphthyl-phosphate
      (8) β-naphthyl-valerate
      (9) 4-methoxyleucine-β-naphthylamide
      (10) glycine-β-naphthylamide 2. A method for the rapid identification of microorganisms comprising the steps of:
   a. Adding a predetermined amount of a salt solution containing a microorganism to be identified to a solution containing a detector reagent comprising fast blue BB (Na Salt) and a stock solution of tris base, sodium lauryl sulfate, hydrochloric acid "%, 2-methoxy ethanol and water, a buffer, selected from the group consisting of tris-HCl, tris-malate, monopotassium phosphate and dipotassium phosphate in a polyvinyl alcohol and a substrate and incubating at about 35° C. for up to five hours and comparing the positive and negative reactions with an identification chart, said substrate being selected from the group consisting of:
      (1) β-naphthyl-β,D-galactopyranoside
      (2) N-L-λ-glutamyl-β-naphthylamide
      (3) L-hydroxyproline-β-naphthylamide
      (4) L-serine-β-naphthylamide
      (5) L-arginine-β-naphthylamide
      (6) glycine-glycine-β-naphthylamide
      (7) β-naphthyl-phosphate
      (8) β-naphthyl-valerate
      (9) 4-methoxyleucine-β-naphthylamide
      (10) glycine-β-naphthylamide 3. A device for the rapid identification of *Neisseria gonorrhoeae* in a specimen containing only one of *N. gonorrhoeae, N. meningitidis* or *N. lactamica* comprising:
   a. a supporting base;
   b. at least two reaction chambers fixedly supported by said base;
   c. a dried substrate disposed in each of said reaction chambers being one of each of β-naphthyl-β-D-galactopyranoside, and L-hydroxyproline-β-naphthylamide; and
   d. a dried buffer selected from the group consisting of tris-HCl, tris-malate, monopotassium phosphate, dipotassium phosphate in a polyvinyl alcohol, N-tris-(hydroxymethyl) methyl-3-amino-propane sulfonate, N-2-hydroxyethyl-piperazine-N'-2-ethane sulfonate, N-2-hydroxyethylpiperazine-N'-3-propane sulfonate, cyclohexylaminoethane sulfonic acid, sodium carbonate, potassium carbonate, sodium borate and potassium borate disposed in each of said reaction chambers;
   whereby in use, a negative reaction in said reaction chamber containing β-naphthyl-β-D-galactopyranoside and a positive reaction in said reaction chamber containing L-hydroxyproline-β-naphthylamide identifes *N. gonorrhoeae.*

4. A device according to claim 3 for the rapid identification of *Neisseria gonorrhoeae* in a specimen containing only one of *N. gonorrhoeae, N. meningitidis* or *N. lactamica* comprising:
   a. a supporting base;
   b. at least two reaction chambers fixedly supported by said base;
   c. a dried substrate disposed in each of said reaction chambers being one of each of β-naphthyl-β-D-galactopyranoside, and L-hydroxyproline-β-naphthylamide; and
   d. a dried buffer disposed in each of said reaction chambers; said buffer selected from the group consisting of tris-HCl, tris-malate, monopotassium phosphate and dipotassium phosphate in a polyvinyl alcohol;
   whereby in use, a negative reaction in said reaction chamber containing β-naphthyl-β-D-galactopyranoside and a positive reaction in said reaction chamber containing L-hydroxyproline-β-naphthylamide identifies *N. gonorrhoeae.*

5. A device for the rapid identification of *Neisseria gonorrhoeae* in a specimen containing only one of *N. gonorrhoeae, N. meningitidis* or *N. lactamica* comprising
   a. a supporting base;
   b. at least three reaction chambers fixedly supported by said base;
   c. a dried substrate disposed in each of said reaction chamber being at least one of each of
      1. β-naphthyl-β,D-galactopyranoside;
      2. N-L-λ-glutamyl-β-naphthylamide;
      3. L-hydroxyproline-β-naphthylamide; and
   d. a dried buffer selected from the group consisting of tris-HCl, tris-malate, monopotassium phosphate, dipotassium phosphate in polyvinyl alcohol, N-tris-(hydroxymethyl) methyl-3-aminopropane sulfonate, N-2-hydroxyethylpiperazine-N'-2-ethane sulfonate, N-2-hydroxyethylpiperazine-N'-3-propane sulfonate, cyclohexylaminoethane sulfonic acid, sodium carbonate, potassium carbonate, sodium borate and potassium borate disposed in each of said reaction chamber;

whereby in use, a positive reaction in said reaction chamber containing L-hydroxyproline-β-naphthylamide and a negative reaction in both of said other reaction chambers identifies *Neisseria gonorrhoeae*.

6. A device as defined in claim 5 in which said buffer is selected from the group consisting of tris-HCl, tris-malate, monopotassium phosphate and dipotassium phosphate in a polyvinyl alcohol.

7. A device for the rapid identification of *Neisseria gonorrhoeae* and *Neisseria meningitidis* comprising:
  a. A supporting base;
  b. A plurality of reaction chambers fixedly supported by said base;
  c. From 1 to 500 nanomoles per chamber of a buffer selected from the group consisting of tris-HCl, tris-malate and phosphate compositions containing $K_2HPO_4$, $KH_2PO_4$ and a polyvinyl alcohol N-tris (hydroxymethyl) methyl-3-aminopropane sulfonate, N-2-hydroxyethylpiperazine-N'-2-ethane sulfonate, N-2-hydroxyethylpiperazine-N'-3-propane sulfonate, cyclohexylaminoethane sulfonic acid, sodium carbonate, potassium carbonate, sodium borate and potassium borate; and
  d. A dried substrate disposed in each of said reaction chambers consisting of 25 to 50 nanomoles per chamber of a member selected from the group consisting of:
    (1) β-naphthyl-β,D-galactopyranoside
    (2) N-L-λ-glutamyl-β-naphthylamide
    (3) L-hydroxyproline-β-naphthylamide
    (4) L-serine-β-naphthylamide
    (5) L-arginine-β-naphthylamide
    (6) glycine-glycine-β-naphthylamide
    (7) β-naphthyl-phosphate
    (8) β-naphthyl-valerate
    (9) 4-methoxyleucine-β-naphthylamide
    (10) glycine-β-naphthylamide 8. A device as defined in claim 7 wherein there are ten reaction chambers.

* * * * *